United States Patent
Li et al.

(10) Patent No.: US 9,988,466 B2
(45) Date of Patent: Jun. 5, 2018

(54) BENZOCROWN ETHER GRAFT POLYMER WITH LITHIUM ISOTOPIC SEPARATION EFFECT AND PREPARATION METHOD THEREOF

(71) Applicant: TIANJIN POLYTECHNIC UNIVERSITY, Tianjin (CN)

(72) Inventors: Jianxin Li, Tianjin (CN); Feng Yan, Tianjin (CN); Benqiao He, Tianjin (CN); Hong Wang, Tianjin (CN)

(73) Assignee: TIANJIN POLYTECHNIC UNIVERSITY, Tianjin (CN)

( * ) Notice: Subject to any disclaimer, the term of this patent is extended or adjusted under 35 U.S.C. 154(b) by 319 days.

(21) Appl. No.: 14/612,012

(22) Filed: Feb. 2, 2015

(65) Prior Publication Data

US 2015/0152201 A1  Jun. 4, 2015

Related U.S. Application Data

(63) Continuation of application No. PCT/CN2013/080433, filed on Jul. 30, 2013.

(30) Foreign Application Priority Data

Aug. 3, 2012 (CN) .......................... 2012 1 0274233
Aug. 3, 2012 (CN) .......................... 2012 1 0274356

(51) Int. Cl.
| | | |
|---|---|---|
| B01D 59/22 | (2006.01) | |
| C08F 8/00 | (2006.01) | |
| C07D 323/00 | (2006.01) | |
| C08G 83/00 | (2006.01) | |
| C08L 101/00 | (2006.01) | |
| B01J 20/26 | (2006.01) | |
| C08G 65/48 | (2006.01) | |
| C08G 75/20 | (2016.01) | |
| C08G 75/23 | (2006.01) | |

(52) U.S. Cl.
CPC .............. C08F 8/00 (2013.01); B01D 59/22 (2013.01); B01J 20/265 (2013.01); C07D 323/00 (2013.01); C08G 65/48 (2013.01); C08G 75/20 (2013.01); C08G 75/23 (2013.01); C08G 83/00 (2013.01); C08L 101/005 (2013.01); C08G 2650/40 (2013.01)

(58) Field of Classification Search
CPC ............................ B01D 59/22; C07D 323/00
See application file for complete search history.

(56) References Cited

U.S. PATENT DOCUMENTS

| | | | |
|---|---|---|---|
| 4,600,566 A | 7/1986 | Fujine et al. | 423/179.5 |
| 2012/0270741 A1* | 10/2012 | Moola | C07K 1/047 506/6 |

FOREIGN PATENT DOCUMENTS

| | | |
|---|---|---|
| CN | 1186506 A | 7/1998 |
| CN | 102786616 A | 11/2012 |
| CN | 102911372 A | 2/2013 |
| JP | 56-047406 A | 4/1981 |
| JP | 2005-254230 A | 9/2005 |

OTHER PUBLICATIONS

Zhan et al Chemical Journal of Chinese Universities vol. 5, No. 6 1984 pp. 802-806.*
Anzai et al. Makromol. Chem. Rapid Commun. 3, 55-58 (Year: 1982).*
Fang, Shengqiang et al., "Lithium Isotope Effect in the Extraction Systems of Crown Ethers—Effect of Mixed Salts of Lithium" Journal of Isotopes, vol. 7, No. 3, (Aug. 1994), pp. 168-171.
Kim, D. W. et al., "Separation of Lithium Isotopes by Aminobenzo-15-Crwon-5 Bonded Merrifield Resin" Journal of Radio analytical and Nuclear Chemistry, vol. 245, No. 3, (2000), pp. 571-574.
Peng, Chang-Hong et al., "Synthesis and Structure Characterization of Chitosan-Crown Ethers" Polymer Materials Science and Engineering, vol. 9, No. 2, (Mar. 2003), pp. 93-96.
Zhan, Caimao et al., "Syntheses of Phenol-Formaldehyde and Acetal Types Polymeric Crown Ethers Containing Benzo-15-Crown-5 and Their Complexing and Catalytic Properties" Chemical Journal of Chinese Universities, vol. 5, No. 6, (1984), pp. 802-806.
Zhou, Qingye et al., "Synthesis and Properties about Crown Ether" Ion Exchange and Adsorption, vol. 12, No. 3, (1996), pp. 271-286.
International Search Report of corresponding international PCT application No. PCT/CN2013/080433, dated Nov. 7, 2013.

* cited by examiner

Primary Examiner — Mark S Kaucher
(74) Attorney, Agent, or Firm — J.C. Patents

(57) ABSTRACT

Disclosed in the present invention is a benzocrown ether graft polymer with a lithium isotopic separation effect and a preparation method thereof. The polymer is a benzocrown ether graft polymer formed by the linkage of chemical bonds, which takes the main chain of a polymer containing chloromethyl group, chloroformyl group or hydroxyl group as main chain, and takes a benzocrown ether as pendant group. The preparation process of the polymer comprises the following steps: preparing polymer solution with certain concentration by dissolving a polymer containing chloromethyl group, chloroformyl group or hydroxyl group in a solvent; then blending a catalyst and a benzocrown ether containing carboxyl group or aldehydyl group and dissolving in the polymer solution containing hydroxyl group, or blending an acid-binding agent and a benzocrown ether containing amino group or hydroxyl group and dissolving in the polymer solution containing chloromethyl group or chloroformyl group, reacting at a certain temperature and for a certain time, linking the benzocrown ether to the main chain of polymer by chemical bonds, and precipitating by adding a precipitating agent to obtain the graft polymer. The grafting polymer has excellent characteristic of lithium isotopic separation.

9 Claims, 4 Drawing Sheets

BENZOCROWN ETHER GRAFT POLYMER WITH LITHIUM ISOTOPIC SEPARATION EFFECT AND PREPARATION METHOD THEREOF

CROSS-REFERENCE TO RELATED APPLICATIONS

This application is a continuation of International Application No. PCT/CN2013/080433, filed on Jul. 30, 2013, which claims the priority benefit of China Patent Application No. 201210274233.1, filed on Aug. 3, 2012 and China patent application No. 201210274356.5, filed on Aug. 3, 2012. The contents of the mentioned applications are hereby incorporated by reference in their entireties.

FIELD OF THE INVENTION

The present invention relates to the field of lithium isotopic separation, particularly to a benzocrown ether graft polymer with lithium isotopic separation effect and preparation method thereof.

BACKGROUND OF THE INVENTION

Natural lithium consists of two isotopes, $^6$Li and $^7$Li, with respective abundances of 7.52% and 92.48%. $^6$Li isotope has high ability to capture slow-moving neutrons. When a compound synthesized with isotope $^6$Li and deuterium, lithium deuteride, is bombarded by neutrons, a strong thermonuclear reaction occurs with a large amount of energy generation. $^7$Li isotope with a tiny thermal neutron absorption cross section (0.037b), can be used as a reactor core coolant for nuclear fusion reactor and a heat-carrying agent for thermal conduction. Thus, it can be seen that lithium isotopes, $^6$Li and $^7$Li, respectively have very important applications in nuclear energy. The separation and production of high purity lithium isotopes are related to the security of national energy and the implementation of sustainable development strategies.

Throughout the domestic and overseas methods by which $^6$Li and $^7$Li are separated from natural lithium, they can be roughly classified into chemical methods and physical methods. Chemical methods include lithium-mercury exchange, ion exchange chromatography, extraction, fractional crystallization, fractional precipitation and the like; physical methods include electromagnetic method, molten salt electrolysis, electron mobility, molecular distillation, laser separation and the like. Currently, only lithium-mercury method has been used for industrial production, due to its advantage in separation coefficient of lithium isotopes, basically around 1.05; in high exchange rate, with only a few seconds of half time of exchange under severe countercurrent condition; and in that two convective phases are prone to be formed in the system, being useful for the design and cascading of processes. However, there is also a great disadvantage in lithium-mercury method for separating lithium isotopes, that is to say, a large amount of mercury used in separation process will cause environmental and safety problems. Factories using lithium-mercury method to separate lithium isotopes in European and American countries have been partially closed; various countries are actively and secretly searching for a green and efficient method for separating lithium isotopes.

Since it has been found that a crown ether can selectively form a complex with a metal ion, especially an alkali metal ion, in accordance with the size of ring, related research on lithium isotope separation are rapidly carried out. Since $^7$Li and $^6$Li have different ionic radii, as well as their different densities of surface charge, there is a difference in adsorption capacity of crown ether between them. Based on this fact, different systems are formed for crown ethers to separate lithium isotopes, mainly including crown ether liquid-liquid extraction and crown ether resin chromatography. The crown ether extraction is a chemical exchange method which uses a crown ether as a neutral chelating extractant, wherein the extraction and separation of lithium isotopes need to undergo three steps, namely extraction, exchange and counter-extraction. The extraction and counter-extraction steps achieve the phase-transfer and counter-flow of materials, while the exchange step achieves the exchange and enrichment of isotopes. The equation of lithium isotope exchange can be expressed as:

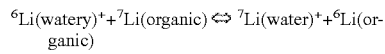

From Oct. 30 to Nov. 2, 1979, in the conference held in the United States on separation science and separation technology for energy application, Jepson from Monsanto made a report on chemical exchange of lithium isotopes by using macrocyclic polyethers. The author determined the separation factors of single-stage equilibria in two-phase chemical exchanges for enriching lithium isotopes in several systems. In the systems studied, $^6$Li are all enriched in the organic phases, the separation factors of single-stage equilibria vary from a minimum value of $\alpha=1.0086\pm0.0023$ to a maximum value of $\alpha=1.041\pm0.006$. This result indicates that Li-cryptand (2.2.1) systems have isotopic separation factors close to lithium-mercury systems, and crown ether systems have great flexibilities in complexing ligands, solvents and counterions. Therefore, such systems provide a new clue for the separation of lithium isotopes. The research on benzo-15-crown-5 derivative system is reported in Shengqiang Fang, Li'an Fu, et. al., *Journal of isotopes*, 1994, 7(3):168-170, and it is proposed that factors affecting the lithium isotopic separation effect in crown ether system include the inner structure of crown ether, the side group of crown ether, the concentration of crown ether, the organic solvent, the anion of lithium salt, the concentration of lithium salt and the temperature. Thus it can be seen that the separation of lithium isotopes by crown ether has a good separation effect; just regarding the separation factor, it is the most promising method for lithium isotopic separation. However, the aforesaid crown ether extraction system mainly uses small molecule crown ethers, hence there would be some problems resulted from such small molecule crown ethers in the application process, such as difficulties in counter-extraction and re-use, expensive prices, some environment pollutions caused by the usage of a large amounts of organic solvents and the like. A good way to solve the above problems is to achieve the loading of crown ether compounds on polymers as carriers.

Disclosed in CN1186506A is a preparation method of water-soluble polymer, which relates to a water-soluble polymer wherein polyvinyl alcohol is grafted with 15-crown-5 ether, but such material is not intended for lithium isotopic separation, and the grafted structure 15-crown-5 does not contain a benzene ring as electron-donating group, thus it has a relatively weak ability of lithium isotopic separation. Disclosed in U.S. Pat. No. 4,600,566A (2006) is a lithium isotope separation method by chromatographic separation based on cryptand-grafted styrene-divinylbenzene resin. This method involves cryptand resin in lithium isotope separation process between solid-liquid two phases, since water molecules are not present in the system, the lithium ion-hydration effect is eliminated, the single-stage separation factor of resin reaches 1.03-1.06, lithium-6 is enriched in resin phase. However, the high energy in complexing of cryptand with lithium ions causes a new problem for desorption of lithium ions, which limits the reusability of resin material. It is reported in Kim et. al., *Journal of Radioanalytical and Nuclear Chemistry*, 2000, 245:571-574 that amino-benzo-15-crown-5 grafted Merrifield peptide resin is used to separate lithium isotopes. The method results in enriched lithium-7 in resin phase, reaching a separation factor of 1.026. However, since the particle size of resin is too small (50-100 μm), the adsorption and desorption of isotopes has a low efficiency.

SUMMARY OF THE INVENTION

For the deficiencies of the prior art, the object of the present invention is to provide a benzocrown ether graft polymer with lithium isotopic separation effect and preparation method thereof.

1.1 The present invention provides a graft polymer with lithium isotopic separation effect, the graft polymer comprises main chain and pendant group, taking the main chain of a polymer containing chloromethyl group or chloroformyl group as main chain, the polymer mainly is polysulfone, polyether sulfone, polystyrene, polyacrylonitrile, or polyether-ether-ketone (the polymer containing chloromethyl group or chloroformyl group mainly is polysulfone, polyether sulfone, polystyrene, polyacrylonitrile, or polyether-ether-ketone containing chloromethyl group or chloroformyl group), the pendant group is a benzocrown ether.

The graft polymer is obtained by the reaction of polymer containing chloromethyl group or chloroformyl group and benzocrown ether containing amino or hydroxyl functional group.

The benzocrown ether used is one of amino benzo macrocyclic crown ethers and hydroxyl benzo macrocyclic crown ethers, their general structures are shown as follows:

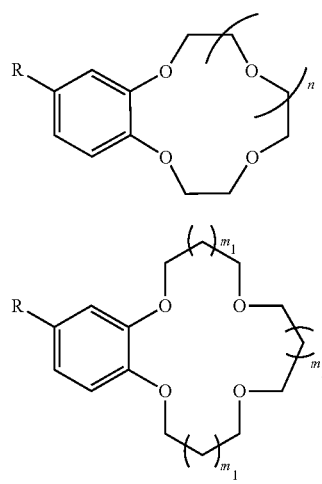

(wherein n is equal to 1, 2, 3 or 4, $m_1$ and $m_2$ are respectively equal to 0 or 1, R group is selected from the group consisting of —$NH_2$ and —OH.)

The content of pendant group in the benzocrown ether graft polymer with lithium isotopic separation effect is 0.1~2.0 mmol/g. After liquid-solid extraction between benzocrown ether and lithium salt in organic solution, the graft polymer, as solid phase, enriches lithium-6 or lithium-7, with a single-stage separation factor of 1.006~1.068.

A preparation method of the benzocrown ether graft polymer is shown as follows: firstly, preparing polymer solution with a certain concentration by dissolving a polymer containing chloromethyl group or chloroformyl group (the polymer containing chloromethyl group or chloroformyl group mainly is polysulfone, polyether sulfone, polystyrene, polyacrylonitrile, or polyether-ether-ketone containing chloromethyl group or chloroformyl group) in a solvent; then blending an acid-binding agent and a benzocrown ether containing amino or hydroxyl functional group (amino benzocrown ether or hydroxyl benzocrown ether) and dissolving in the polymer solution, covalently bonding the benzocrown ether to the main chain of polymer by SN1 reaction at a certain temperature and for a certain time, and precipitating the graft polymer from the polymer solution by using a precipitating agent to obtain the graft polymeric material.

In the present invention, the benzocrown ethers containing amino functional group include the followings:

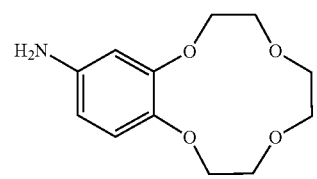

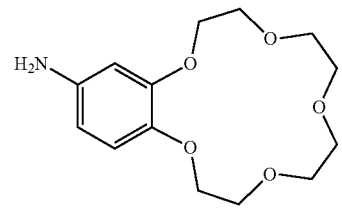

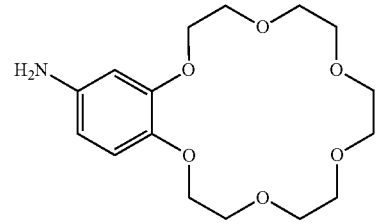

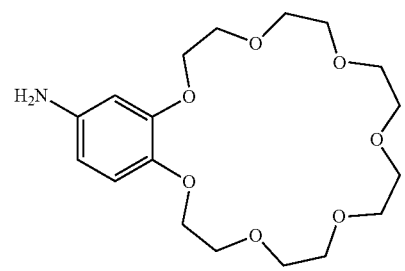

(5)
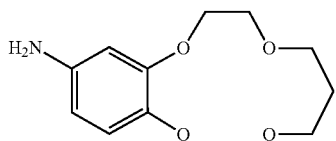

(6)
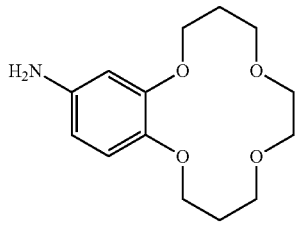

(7)
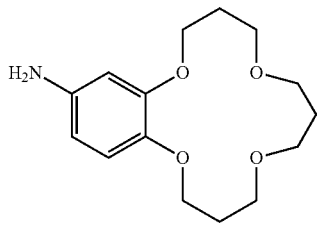

In the present invention, the benzocrown ether containing hydroxyl functional group includes the followings:

(8)
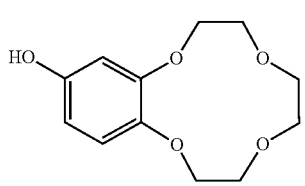

(9)
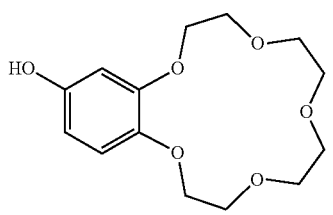

(10)
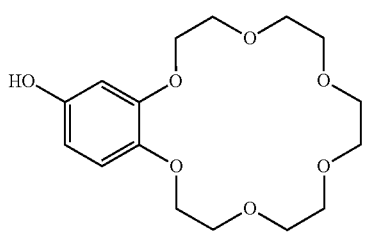

(11)
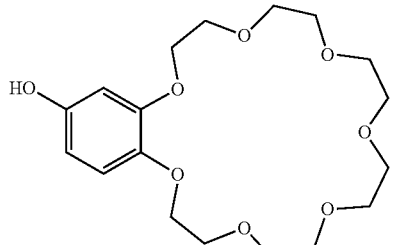

(12)
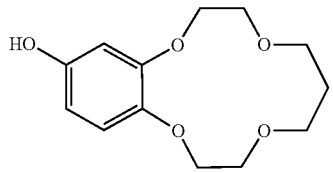

(13)
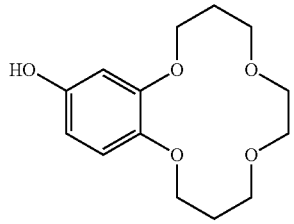

(14)
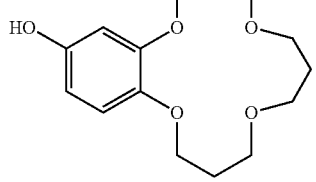

One of N,N-dimethyl formamide (DMF), 1,4-dioxane, dimethyl sulfoxide and N,N-dimethyl acetamide (DMAA) is selected as solvent; one of anhydrous potassium carbonate, anhydrous sodium carbonate, anhydrous sodium bicarbonate and triethylamine is selected as acid-binding agent; one of crown ether compounds represented by amino or hydroxyl benzo macrocyclic crown ethers is selected as functionalized benzocrown ether.

In the reaction system, the concentration of polymer solution containing chloromethyl group or chloroformyl group is 10.0 g/L~100.0 g/L, the mass ratio of polymer to benzocrown ether is 1:1~5:1; the amount of acid-binding agent is sufficient to be able to catalyze the substitution reaction. The benzocrown ether molecule is covalently bonded to the main chain of polymer by SN1 reaction at a temperature of 50~80° C. and for a reactive time of 5~24 h, and a precipitating agent is used to precipitate the graft polymer from the polymer solution to obtain the graft polymer material. The precipitating agent used for precipitating polymer after reaction is one of methanol, ethanol, n-butanol and acetone.

1.2 The present invention provides a graft polymer with lithium isotopic separation effect, the graft polymer comprises main chain and pendant group, taking the main chain of a polymer containing hydroxyl as main chain, the polymer containing hydroxyl mainly is polyvinyl alcohol, polyethylene-vinyl alcohol, chitosan, chitin or cellulose with a hydroxyl substitution degree of lower than 3 in glucose unit, the pendant group is a benzocrown ether.

The crown ether graft polymer is obtained by the reaction of polymer containing hydroxyl and benzocrown ether containing carboxyl or aldehydyl functional group.

The benzocrown ether used is one of formyl benzo macrocyclic crown ethers and carboxyl benzo macrocyclic crown ethers, their general structures are shown as follows:

(I)

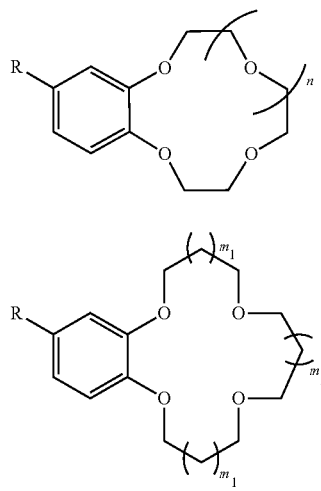

(II)

(wherein n is equal to 1, 2, 3 or 4, $m_1$ and $m_2$ are equal to 0 or 1, R is selected from the group consisting of —CHO and —COOH.)

The content of pendant group in the graft polymer with lithium isotopic separation effect is 0.1~3.0 mmol/g. After liquid-solid extraction, the graft polymer, as solid phase, enriches lithium-6 or lithium-7, with a single-stage separation factor of 1.008~1.052.

The preparation method of the graft polymer is shown as follows: firstly, preparing polymer solution with a certain concentration by dissolving a polymer containing hydroxyl (the polymer mainly is polyvinyl alcohol, polyethylene-vinyl alcohol, chitosan, chitin or cellulose with a hydroxyl substitution degree of lower than 3 in glucose unit) in a solvent; then blending a catalyst and a benzocrown ether containing carboxyl or aldehydyl functional group and dissolving in the polymer solution, covalently bonding the benzocrown ether to the main chain of polymer by chemical grafting reaction at a certain temperature and for a certain time, and precipitating the graft polymer from the polymer solution by using a precipitating agent to obtain the graft polymeric material.

In the present invention, the benzocrown ethers containing formyl functional group include the followings:

(15)

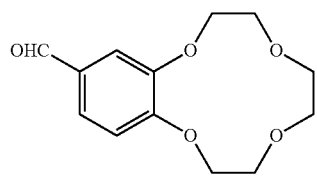

(16)

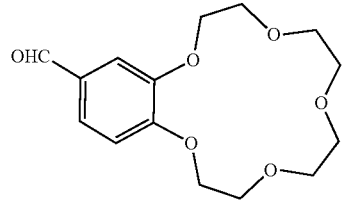

(17)

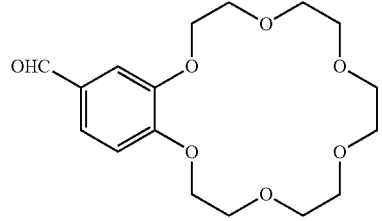

(18)

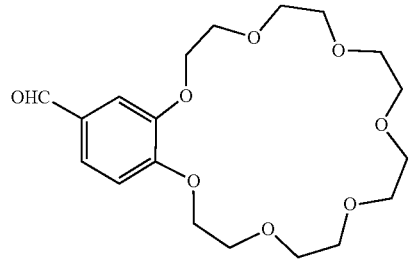

(19)

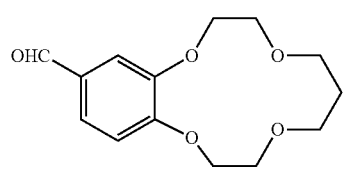

(20)

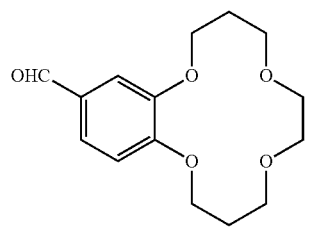

(21)

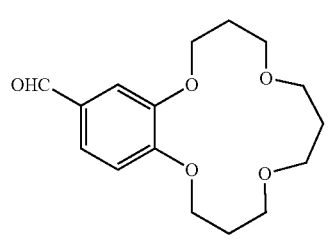

In the present invention, the benzocrown ethers containing carboxyl functional group include the followings:

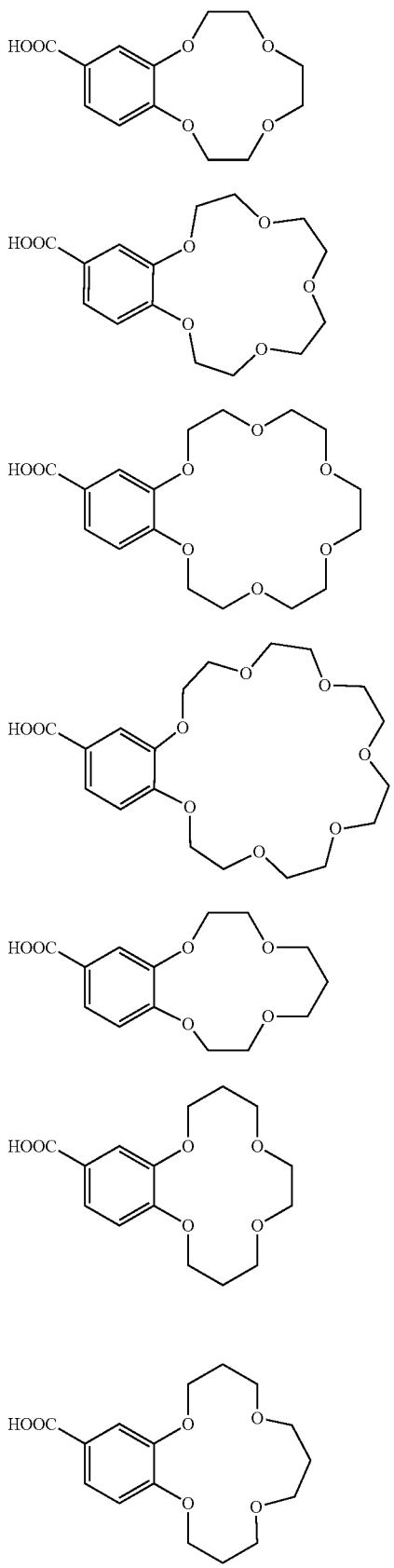

One of distilled water and dimethyl sulfoxide is selected as solvent; one of $H_2SO_4$, HF, HCl, p-toluenesulfonic acid, $FeCl_3$, $SnCl_2$, $NaHSO_4$, $CuSO_4$ and dibutyl tin dilaurate is selected as catalyst.

In the reaction system, the concentration of polymer solution containing hydroxyl is 10.0 g/L~100.0 g/L, the mass ratio of polymer to benzocrown ether is 0.1:1~5:1, the mass ratio of polymer to catalyst is 0.5:1~50:1.

The benzocrown ether is covalently bonded to the main chain of polymer by chemical grafting reaction at a temperature of 50~130° C. and for a reactive time of 1~24 h, and a precipitating agent is used to precipitate the graft polymer from the polymer solution to obtain the graft polymer material.

The precipitating agent used for precipitating polymer after reaction is one of methanol, ethanol, n-butanol and acetone.

Compared with the prior art, the graft polymer of the present invention is easy to be made into powder, granule or thin film; meanwhile, it is easily soluble in organic solvents, thus it can be prepared into a microporous material having a well developed micropore structure and a high specific surface so as to achieve efficient separation and continuous production of lithium isotopes. The graft polymer of the present invention has the following advantages like high loading amount of crown ether, excellent separation efficiency, mild operating conditions, green and environmentally friendly, and simple preparation process.

Figure 1:
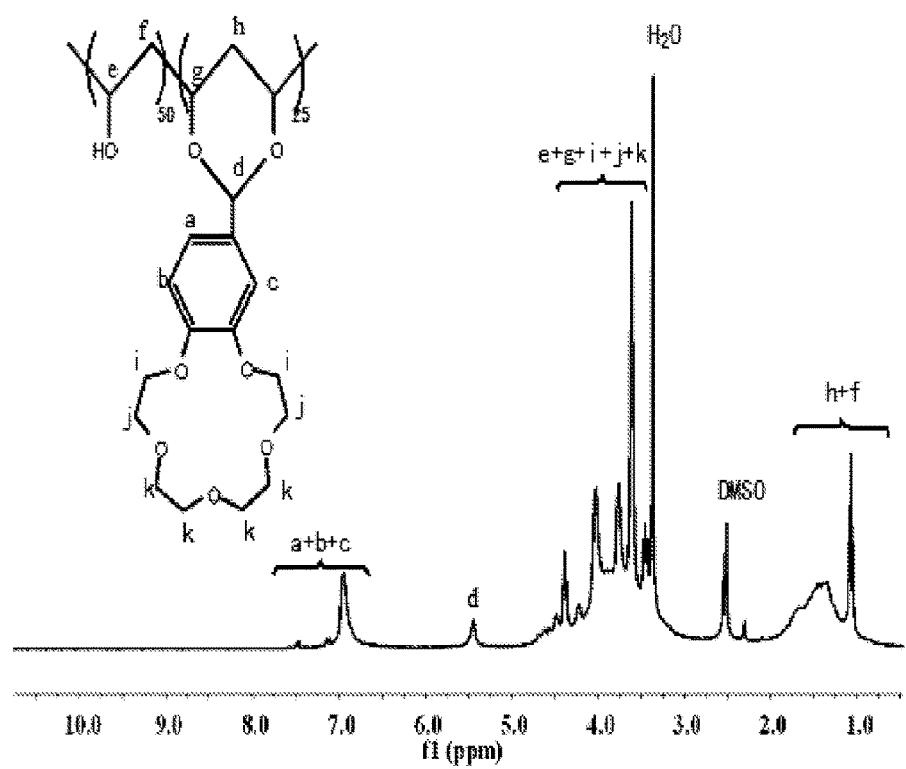
FIG. 1 shows the structural formula and $^1$H-NMR spectrum of 4-formyl benzo-15-crown-5 grafted polyvinyl alcohol.

As can be seen from FIG. 1, the hydrogen atoms a, b, c on benzene ring in the compound correspond to the peaks at a chemical shift of 6.8 ppm-7.5 ppm, the peak d at a chemical shift of 5.4 ppm is assigned to the methine proton formed after acetalization of aldehydyl group, the peaks at a chemical shift of 1-1.8 ppm are derived from the methylene protons in the main chain of polyvinyl alcohol. It can be proved that small molecule crown ether has been grafted to the main chain of polyvinyl alcohol molecule by chemical reaction.

Figure 2:
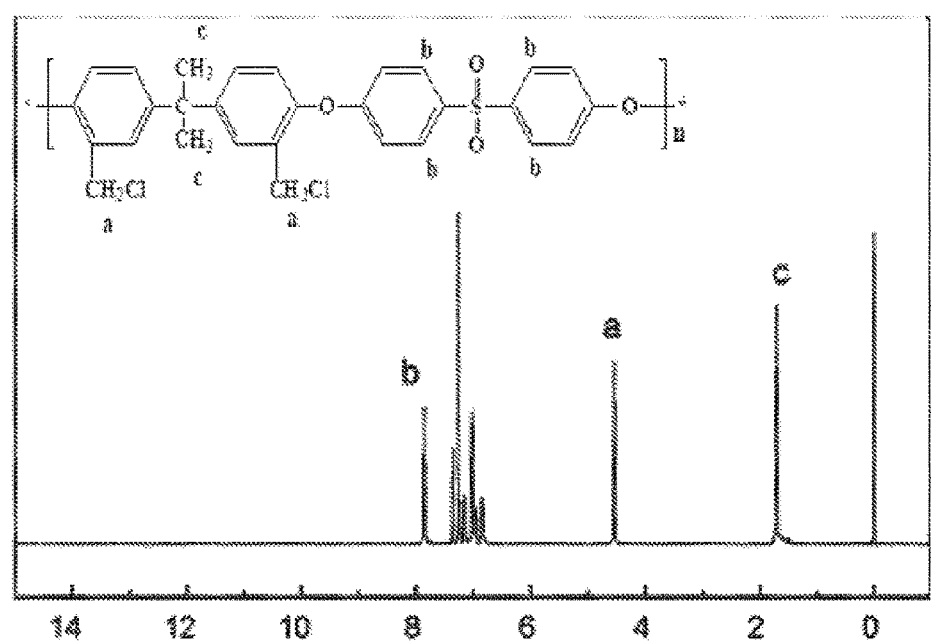

FIG. 2 shows the NMR spectrum of chloromethylated polysulfone polymer.

As can be seen from FIG. 2, the peak at a chemical shift of δ 1.70 ppm is resonance absorption peak of protons in methyl (—$CH_3$) of polysulfone molecule; various peaks at a chemical shift of δ 6.90~7.50 ppm correspond to resonance signals of various protons on benzene rings; the peak at a chemical shift of δ 7.83 ppm is resonance absorption peak of protons which are adjacent to sulfone group on benzene ring, while the resonance absorption peak appearing at a chemical shift of δ 4.53 is the peak of protons in chloromethyl (—$CH_2Cl$) grafted to polysulfone molecule. It can be seen that chloromethylated polysulfone has been successfully prepared.

Figure 3:
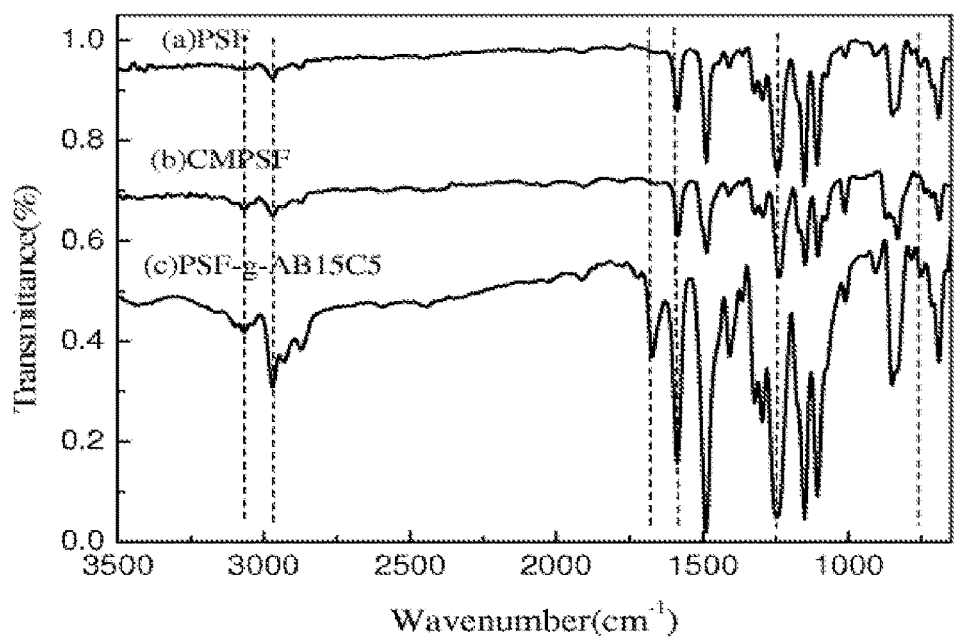

FIG. 3 shows the infrared spectra of polysulfone (PSF), chloromethylated polysulfone (CMPSF) and 4-amino benzo-15-crown-5 grafted polysulfone (PSF-g-AB15C5) polymer in Example 11.

As can be seen from FIG. 3, in the infrared spectrum of polysulfone (PSF), the absorption peak at 1589.7 cm$^{-1}$ is stretching vibration peak of C—H bond in aromatic hydrocarbons; while the absorption peak at 1360.8 cm$^{-1}$ is symmetric vibration absorption peak of S=O bond; the absorption peaks at 1239.9 cm$^{-1}$ is asymmetric stretching vibration peak of

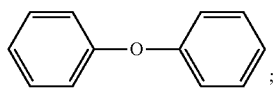 [SMILES: c1ccc(Oc2ccccc2)cc1]

;

the characteristic peak at 1065 cm$^{-1}$ is symmetric stretching vibration absorption peak of sulfoxide group; the characteristic peaks at 1325 cm$^{-1}$ and 1298 cm$^{-1}$ are asymmetric stretching vibration absorption peaks of sulfoxide group; the characteristic absorption peaks at 1580 cm$^{-1}$ and 1478 cm$^{-1}$ are characteristic absorption peaks of benzene ring. Comparing the infrared absorption spectrum of chloromethylated polysulfone (CMPSF) with the infrared absorption spectrum of PSF, in the infrared spectrum of CMPSF, two characteristic absorption peaks newly appears at 750 cm$^{-1}$ and 880 cm$^{-1}$, wherein the absorption peak at 750 cm$^{-1}$ is stretching vibration peak of C—Cl bond in chloromethyl (—CH$_2$Cl), and the characteristic absorption peak at 880 cm$^{-1}$ is characteristic absorption peak of benzene ring after occurring triple substitution on 1-, 2- and 4-position thereof; these changes show that, in the presence of 1,4-bis(chloromethoxy)butane, polysulfone has undergone a chemical modification to generate chloromethylation-modified CMPSF. Compared to the infrared absorption spectrum of CMPSF, in the infrared absorption spectrum of PSF-g-AB15C5 polymer, the absorption peak at 750 cm$^{-1}$ disappears, while new absorption peaks appear at 1130 cm$^{-1}$ and 1680 cm$^{-1}$, and these two peaks respectively correspond to characteristic absorption peaks of C—O—C bond and C—N bond in crown ether molecule. This shows that 4-amino benzo-15-crown-5 (AB15C5) molecule has been grafted to polysulfone molecule, namely achieving the loading of crown ether, and obtaining PSF-g-AB15C5 polymer.

Figure 4:
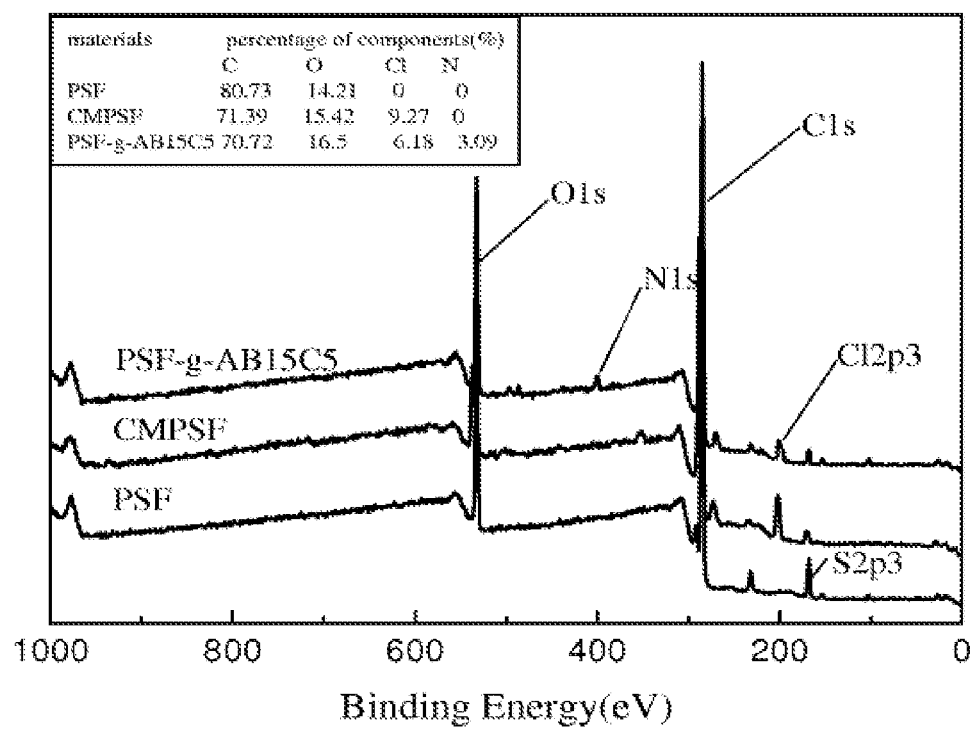

FIG. 4 shows the elemental analysis and X-ray diffraction spectroscopy (XPS) of polysulfone (PSF), chloromethylated polysulfone (CMPSF) and 4-amino benzo-15-crown-5 grafted polysulfone (PSF-g-AB15C5) polymer of Example 11.

It can be seen from percentage contents of various chemical elements in the surface of polymeric materials that the main elements in the surface of PSF material are carbon, oxygen, and sulfur, without chlorine or nitrogen element; in addition to carbon, oxygen, and sulfur, CMPSF material also comprises chlorine element in its surface, wherein the content of chlorine element is 9.27%; while in PSF-g-AB15C5 polymer material, in addition to carbon, oxygen, sulfur, and chlorine, nitrogen element newly appears, and the content of chlorine element is reduced from 9.27% of that in CMPSF to 6.18%, it can be seen that SN1 reaction has occurred between parts of the chloromethyl in CMPSF and AB15C5, and that crown ether molecule has been grafted to polysulfone molecule.

In addition, it can be seen from XPS spectra of PSF, CMPSF and PSF-g-AB15C5 polymeric material that, in XPS spectra of CMPSF, a scattering peak appears at 200 eV; after consulting the literature, the scattering peak of Cl2p3 just appears at 200 eV, indicating that chlorine element appears in CMPSF material and that the chlorine element is chemically bonded to CMPSF polymer material. It can be proved that polysulfone has been successfully modified and that chlorobenzyl as active group has been introduced into polysulfone molecule. However, compared to the XPS spectra of PSF and CMPSF, in the XPS spectrum of PSF-g-AB15C5 polymeric material, the scattering peak of Cl2p3 appearing at 200 eV is weaker than that in the XPS spectrum of CMPSF, while a new scattering peak appears at 398.4 eV; after consulting the literature, the scattering peak of N1s just appears at 398.4 eV, indicating that nitrogen element is present in PSF-g-AB15C5 polymer in the form of C—N bond, and also reflecting that AB15C5 molecule has really been grafted to polysulfone molecule.

DETAILED DESCRIPTION OF THE INVENTION

The following embodiments would make those skilled in the art better understand the present invention, but not limit the scope of the present invention in any way.

Example 1

The preparation method of 4-formyl benzo-15-crown-5 grafted polyvinyl alcohol is described in detail as follows: 60 mL of 85 g/L aqueous solution of polyvinyl alcohol was taken, in which 1 g of 4-formyl benzo-15-crown-5 (as shown in formula 16) was added in accordance with a mass ratio of polymer to benzocrown ether of 5:1, then 10 g of concentrated hydrochloric acid was added as catalyst in accordance with a mass ratio of polymer to catalyst of 0.5:1 and then uniformly blended; after reacting at a controlled temperature of 80±5° C. for 1 h, the reaction system was poured into ethanol to precipitate. The precipitate was obtained by suction filtration. It is washed with ethanol for several times and dried to afford crown ether grafted polymeric material, wherein the content of pendant group is 1.1 mmol/g. The polymeric material was added into an aqueous solution of lithium chloride to afford polymeric material by means of solid-liquid extraction, wherein the single-stage separation factor is 1.033. The structural formula and $^1$H-NMR spectrum of 4-formyl benzo-15-crown-5 grafted polyvinyl alcohol are shown in FIG. 1.

Example 2

The preparation method of 4-formyl benzo-13-crown-4 grafted polyvinyl alcohol is described in detail as follows: 150 mL of 6.7 g/L aqueous solution of polyvinyl alcohol was taken, in which 10 g of 4-formyl benzo-13-crown-4 (as shown in formula 19) was added in accordance with a mass ratio of polymer to benzocrown ether of 0.1:1, then 1 g of concentrated sulfuric acid was added as catalyst in accordance with a mass ratio of polymer to catalyst of 1:1 and then uniformly blended; after reacting at a controlled temperature of 70±5° C. for 15 h, the reaction system was poured into ethanol to precipitate. The precipitate was obtained by suction filtration. It is washed with ethanol for several times and dried to afford polymer, 4-formyl benzo-13-crown-4 grafted polyvinyl alcohol, wherein the content of pendant group is 3.0 mmol/g. The polymer was added into an aqueous solution of lithium chloride to afford polymer by means of solid-liquid extraction, wherein the single-stage separation factor is 1.043. The polymer obtained in the present example has a structure as follows:

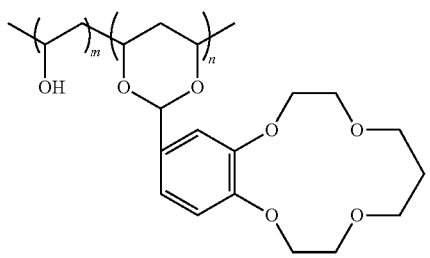

Example 3

The preparation method of 4-formyl benzo-12-crown-4 grafted polyvinyl alcohol is described in detail as follows: 160 mL of 31.3 g/L aqueous solution of polyvinyl alcohol was taken, in which 1 g of 4-formyl benzo-12-crown-4 (as shown in formula 15) was added in accordance with a mass ratio of polymer to benzocrown ether of 5:1, then 0.1 g of concentrated sulfuric acid was added in accordance with a mass ratio of polymer to catalyst of 50:1 and then uniformly blended; after reacting at a controlled temperature of 80±5° C. for 24 h, the reaction system was poured into n-butanol to precipitate. The precipitate was obtained by suction filtration. It is washed with acetone for several times and dried to afford crown ether grafted polymer, wherein the content of pendant group is 0.7 mmol/g. The crown ether grafted polymer was added into an aqueous solution of lithium chloride to afford crown ether grafted polymer by means of solid-liquid extraction, wherein the single-stage separation factor is 1.043.

Example 4

The preparation method of 4-formyl benzo-14-crown-4 grafted polyvinyl alcohol is described in detail as follows: 200 mL of 25 g/L polyvinyl alcohol in dimethyl sulfoxide solution was taken, in which 10 g of 4-formyl benzo-14-crown-4 (as shown in formula 20) was added in accordance with a mass ratio of polymer to benzocrown ether of 0.5:1, then 0.1 g of p-toluenesulfonic acid was added in accordance with a mass ratio of polymer to catalyst of 50:1 and then uniformly blended; after reacting at a controlled temperature of 50±5° C. for 1 h, the reaction system was poured into methanol to precipitate. The precipitate was obtained by suction filtration. It is washed with ethanol for several times and dried to afford crown ether grafted polymer, wherein the content of pendant group is 2.0 mmol/g. The crown ether grafted polymer was added into an aqueous solution of lithium chloride to afford crown ether grafted polymer by means of solid-liquid extraction, wherein the single-stage separation factor is 1.049.

Example 5

The preparation method of 4-carboxyl benzo-18-crown-6 grafted polyethylene-vinyl alcohol is described in detail as follows: 150 mL of 13.3 g/L aqueous solution of polyethylene-vinyl alcohol was taken, in which 2 g of 4-carboxyl benzo-18-crown-6 (as shown in formula 24) was added in accordance with a mass ratio of polymer to benzocrown ether of 1:1, then 0.3 g of $FeCl_3$ was added in accordance with a mass ratio of polymer to catalyst of 1:1 and then uniformly blended; after reacting at a controlled temperature of 125-130° C. for 10 h, the reaction system was poured into iso-propanol to precipitate. The precipitate was obtained by suction filtration. It is washed with ethanol for several times and dried to afford crown ether grafted polymer, wherein the content of pendant group is 2.6 mmol/g. The crown ether grafted polymer was added into an aqueous solution of lithium chloride to afford crown ether grafted polymer by means of solid-liquid extraction, wherein the single-stage separation factor is 1.024.

Example 6

The preparation method of 4-carboxyl benzo-21-crown-7 grafted polyethylene-vinyl alcohol is described in detail as follows: 200 mL of 10 g/L polyethylene-vinyl alcohol in dimethyl sulfoxide solution was taken, in which 0.4 g of 4-carboxyl benzo-21-crown-7 (as shown in formula 25) was added in accordance with a mass ratio of polymer to benzocrown ether of 5:1, then 0.04 g of $SnCl_2$ was added in accordance with a mass ratio of polymer to catalyst of 50:1 and then uniformly blended; after reacting at a controlled temperature of 120-125° C. for 24 h, the reaction system was poured into n-butanol to precipitate. The precipitate was obtained by suction filtration. It is washed with acetone for several times and dried to afford crown ether grafted polymer, wherein the content of pendant group is 0.1 mmol/g. The crown ether grafted polymer was added into an aqueous solution of lithium chloride to afford crown ether grafted polymer by means of solid-liquid extraction, wherein the single-stage separation factor is 1.008.

Example 7

The preparation method of 4-carboxyl benzo-15-crown-5 grafted polyethylene-vinyl alcohol is described in detail as follows: 50 mL of 40 g/L polyethylene-vinyl alcohol in dimethyl sulfoxide solution was taken, in which 0.5 g of 4-carboxyl benzo-15-crown-5 (as shown in formula 23) was added in accordance with a mass ratio of polymer to benzocrown ether of 4:1, then 0.2 g of dibutyl tin dilaurate was added in accordance with a mass ratio of polymer to catalyst of 10:1 and then uniformly blended; after reacting at a controlled temperature of 110-115° C. for 24 h, the reaction system was poured into acetone to precipitate. The precipitate was obtained by suction filtration. It is washed with acetone for several times and dried to afford crown ether grafted polymer 1.6 mmol/g. The crown ether grafted polymer was added into an aqueous solution of lithium chloride to afford crown ether grafted polymer by means of solid-liquid extraction, wherein the single-stage separation factor is 1.036.

Example 8

The preparation method of 4-carboxyl benzo-15-crown-4 grafted polyethylene-vinyl alcohol is described in detail as follows: 40 mL of 50 g/L polyethylene-vinyl alcohol in dimethyl sulfoxide solution was taken, in which 5 g of 4-carboxyl benzo-15-crown-5 (as shown in formula 23) was added in accordance with a mass ratio of polymer to benzocrown ether of 0.4:1, then 0.3 g of $SnCl_4$ was added in accordance with a mass ratio of polymer to catalyst of 6.7:1 and then uniformly blended; after reacting at a controlled temperature of 110-115° C. for 24 h, the reaction system was poured into methanol to precipitate. The precipitate was obtained by suction filtration. It is washed with acetone for several times and dried to afford crown ether grafted polymer, wherein the content of pendant group is 2.4 mmol/g.

The crown ether grafted polymer was added into an aqueous solution of lithium chloride to afford crown ether grafted polymer by means of solid-liquid extraction, wherein the single-stage separation factor is 1.034.

Example 9

The preparation method of 4-carboxyl benzo-14-crown-4 grafted polyethylene-vinyl alcohol is described in detail as follows: 100 mL of 20 g/L polyethylene-vinyl alcohol in dimethyl sulfoxide solution was taken, in which 1.25 g of 4-carboxyl benzo-14-crown-4 (as shown in formula 27) was added in accordance with a mass ratio of polymer to benzocrown ether of 2.5:1, then 8 g of $CuSO_4$ was added in accordance with a mass ratio of polymer to catalyst of 25:1 and then uniformly blended; after reacting at a controlled temperature of 110-115° C. for 3 h, the reaction system was poured into acetone to precipitate. The precipitate was obtained by suction filtration. It is washed with acetone for several times and dried to afford crown ether grafted polymer, wherein the content of pendant group is 1.8 mmol/g. The crown ether grafted polymer was added into an aqueous solution of lithium chloride to afford crown ether grafted polymer by means of solid-liquid extraction, wherein the single-stage separation factor is 1.052.

Example 10

The preparation method of 4-carboxyl benzo-12-crown-4 grafted polyethylene-vinyl alcohol is described in detail as follows: 200 mL of 25 g/mL polyethylene-vinyl alcohol in dimethyl sulfoxide solution was taken, in which 1 g of 4-carboxyl benzo-15-crown-4 (as shown in formula 28) was added in accordance with a mass ratio of polymer to benzocrown ether of 5:1, then 1 g of dibutyl tin dilaurate was added in accordance with a mass ratio of polymer to catalyst of 5:1 and then uniformly blended; after reacting at a controlled temperature of 90-95° C. for 18 h, the reaction system was poured into glycerol to precipitate. The precipitate was obtained by suction filtration. It is washed with ethanol for several times and dried to afford crown ether grafted polymer, wherein the content of pendant group is 2.7 mmol/g. The crown ether grafted polymer was added into an aqueous solution of lithium chloride to afford crown ether grafted polymer by means of solid-liquid extraction, wherein the single-stage separation factor is 1.037.

Example 11

The preparation method of 4-amino benzo-15-crown-5 grafted polysulfone polymeric material is described in detail as follows: 2 g of dried polysulfone was weighed and placed into a four-necked flask, and completely dissolved in dichloromethane, then 5 ml of 1,4-bis(chloromethoxy)butane and 0.5 ml of anhydrous stannic chloride were added and reacted at room temperature for 3 h, and then precipitated in methanol and dried in a vacuum drying oven at 60° C. to afford chloromethylated polysulfone with a substitution degree of about 1.5 (the chemical structural formula and characterization are shown in FIG. 2). 1 g of chloromethylated polysulfone was weighed and dissolved in 100 mL of DMF, 0.2 g of 4-amino benzo-15-crown-5 and 0.010 g of anhydrous potassium carbonate were added and uniformly blended; after reacting at a controlled temperature of 48±2° C. for 5 h, the reaction system was poured into methanol to precipitate. The precipitate was obtained by suction filtration. It is washed with methanol for several times and dried to afford crown ether grafted polysulfone polymeric material, wherein the loading amount of crown ether is 0.1 mmol/g. The graft polymeric material obtained by means of solid-liquid extraction between crown ether grafted polysulfone polymer and lithium chloride in methanol solution has a single-stage separation factor of 1.006 for lithium isotopes. The polymeric material obtained in the present example has a structure as follows:

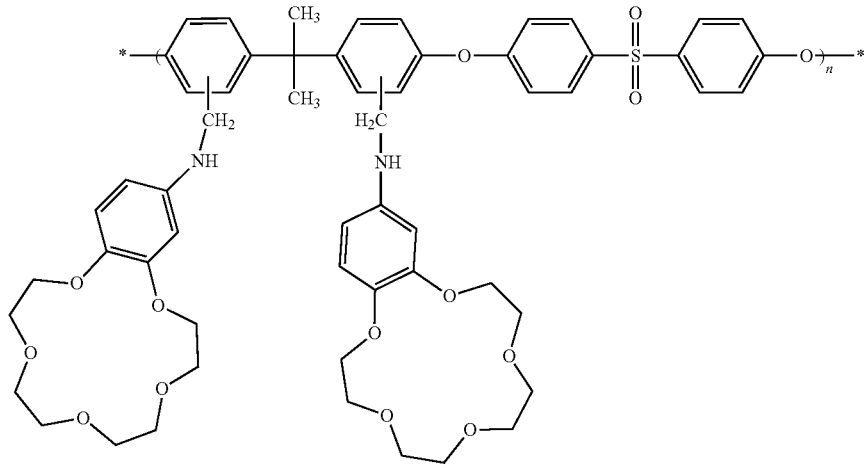

Example 12

The preparation method of 4-hydroxyl benzo-15-crown-5 grafted polysulfone polymer is described in detail as follows: chloromethylated polysulfone with a substitution degree of about 1.5 was obtained by using the same method as above, then 1 g of chloromethylated polysulfone was weighed and dissolved in 10 mL of DMF, 1 g of 4-hydroxyl benzo-15-crown-5 and 0.488 g of anhydrous potassium carbonate were added and uniformly blended; after reacting at a controlled temperature of 75±5° C. for 24 h, the reaction system was poured into methanol to precipitate. The precipitate was obtained by suction filtration. It is washed with methanol for several times and dried to afford graft polymeric material, wherein the loading amount of crown ether is 2.0 mmol/g. The graft polymeric material obtained by means of solid-liquid extraction in Example 11 has a single-stage separation factor of 1.068 for lithium isotopes.

Example 13

The preparation method of 4-amino benzo-12-crown-4 grafted polysulfone polymeric material is described in detail as follows: chloromethylated polysulfone with a substitution degree of about 1.0 was obtained by using the same method as above, then 1 g of chloromethylated polysulfone was accurately weighed and dissolved in 20 mL of DMAA, 0.4 g of 4-amino benzo-12-crown-4 and 0.30 g of triethylamine were added and uniformly blended; after reacting at a controlled temperature of 60±2° C. for 12 h, the reaction system was poured into ethanol to precipitate. The precipitate was obtained by suction filtration. It is washed with ethanol for several times and dried to afford benzocrown ether grafted polysulfone polymeric material, wherein the loading amount of crown ether is 1.0 mmol/g. The polymeric material obtained by means of solid-liquid extraction in Example 11 has a single-stage separation factor of 1.043 for lithium isotopes.

Example 14

The preparation method of 4-hydroxyl benzo-14-crown-4 grafted polysulfone polymeric material is described in detail as follows: chloromethylated polysulfone with a substitution degree of about 1.0 was obtained by using the same method as above, then 1 g of chloromethylated polysulfone was accurately weighed and dissolved in 20 mL of dimethyl sulfoxide, 0.5 g of 4-hydroxyl benzo-14-crown-4 and 0.072 g of anhydrous sodium carbonate were added and uniformly blended; after reacting at a controlled temperature of 70±2° C. for 10 h, the reaction system was poured into n-butanol to precipitate. The precipitate was obtained by suction filtration. It is washed with n-butanol for several times and dried to afford benzocrown ether grafted polysulfone polymeric material, wherein the loading amount of crown ether is 0.8 mmol/g. The polymeric material obtained by means of solid-liquid extraction in Example 11 has a single-stage separation factor of 1.026 for lithium isotopes.

Example 15

The preparation method of 4-amino benzo-18-crown-6 grafted polysulfone polymeric material is described in detail as follows: in a four-necked flask, 6 g of polysulfone was dissolved in 420 ml of chloroform, heated and stirred until it was completely dissolved, then 6 g of trioxane, 0.6 g of anhydrous stannic chloride, 25.5 ml of trimethylchlorosilane solution were added; experimental apparatus is assembled to perform reaction at 60° C. for 72 h. After completing the reaction, the reaction solution was poured into an excess amount of methanol to precipitate, and then the precipitate was obtained by suction filtration. The obtained white solid was washed with methanol for several times and dried in a vacuum drying oven at 60° C. to afford chloromethylated polysulfone with a substitution degree of 0.5. 1 g of chloromethylated polysulfone was accurately weighed and dissolved in 50 mL of 1,4-dioxane, 1 g of 4-amino benzo-18-crown-6 and 0.5 g of anhydrous sodium bicarbonate were added and uniformly blended; after reacting at a controlled temperature of 60±2° C. for 12 h, the reaction system was poured into acetone to precipitate. The precipitate was obtained by suction filtration. It is washed with acetone for several times and dried to afford benzo-18-crown-6 grafted polysulfone polymeric material, wherein the loading amount of crown ether is 0.6 mmol/g. The membrane material obtained by means of solid-liquid extraction in Example 11 has a single-stage separation factor of 1.018.

Example 16

The preparation method of 4-amino benzo-21-crown-7 grafted polysulfone polymeric material is described in detail as follows: chloromethylated polysulfone with a substitution degree of 0.5 was obtained by using the method in Example 5, 1 g of chloromethylated polysulfone was accurately weighed and dissolved in 80 mL of DMAA, 1 g of 4-amino benzo-21-crown-7 and 0.7 g of anhydrous sodium carbonate were added and uniformly blended; after reacting at a controlled temperature of 75±2° C. for 14 h, the reaction system was poured into anhydrous ethanol to precipitate. The precipitate was obtained by suction filtration. It is washed with anhydrous ethanol for several times and dried to afford benzo-21-crown-7 grafted polysulfone polymeric material, wherein the loading amount of crown ether is 0.2 mmol/g. The membrane material obtained by means of solid-liquid extraction in Example 11 has a single-stage separation factor of 1.008.

Example 17

The preparation method of 4-amino benzo-15-crown-5 grafted polyether-ether-ketone polymeric material is described in detail as follows: chloromethylated polyether-ether-ketone with a substitution degree of 1 was obtained by using the method in Example 1, 2 g of chloromethylated polyether-ether-ketone was accurately weighed and dissolved in 100 mL of DMF, 1 g of 4-amino benzo-15-crown-5 and 0.488 g of anhydrous potassium carbonate were added and uniformly blended; after reacting at a controlled temperature of 70±2° C. for 18 h, the reaction system was poured into acetone to precipitate. The precipitate was obtained by suction filtration. It is washed with acetone for several times and dried to afford graft polymeric material, wherein the loading amount of crown ether is 1.2 mmol/g. The graft polymeric material obtained by means of solid-liquid extraction in Example 11 has a single-stage separation factor of 1.046.

Example 18

The preparation method of 4-hydroxyl benzo-15-crown-5 grafted polyether-ether-ketone polymeric material is described in detail as follows: chloromethylated polyether-ether-ketone with a substitution degree of 1 was obtained by using the method in Example 1, 2 g of chloromethylated polyether-ether-ketone was accurately weighed and dissolved in 50 mL of DMF, 0.5 g of 4-hydroxyl benzo-15-crown-5 and 0.25 g of triethylamine were added and uniformly blended; after reacting at a controlled temperature of 70±2° C. for 16 h, the reaction system was poured into methanol to precipitate. The precipitate was obtained by suction filtration. It is washed with methanol for several times and dried to afford crown ether grafted polyether-ether-ketone polymeric material, wherein the loading amount of crown ether is 0.7 mmol/g. The membrane material obtained by means of solid-liquid extraction in Example 11 has a single-stage separation factor of 1.036.

Example 19

The preparation method of 4-amino benzo-15-crown-5 grafted polyether sulfone polymeric material is described in detail as follows: chloromethylated polyether sulfone with a substitution degree of 1 was obtained by using the method in Example 1, 1 g of chloromethylated polyether sulfone was weighed and dissolved in 100 mL of DMF, 1 g of 4-amino benzo-15-crown-5 and 0.488 g of anhydrous potassium carbonate were added and uniformly blended; after reacting at a controlled temperature of 60±2° C. for 5 h, the reaction system was poured into methanol to precipitate. The precipitate was obtained by suction filtration. It is washed with methanol for several times and dried to afford crown ether grafted polyether sulfone polymeric material, wherein the loading amount of crown ether is 1.2 mmol/g. The graft polymeric material obtained by means of solid-liquid extraction between crown ether grafted polyether sulfone polymer and lithium chloride in methanol solution has a single-stage separation factor of 1.056 for lithium isotopes.

Example 20

The preparation method of 4-amino benzo-15-crown-5 grafted polyacrylonitrile material comprises the following steps: a certain amount of polyacrylonitrile was hydrolyzed in 0.5N NaOH aqueous solution at 95° C. for 3 h, then precipitated with ethanol, filtered, and dried; by using 0.5N thionyl chloride (SOCl2) in chloroform solution, it was subjected to chloroacylation reaction at 70° C. for 7 h to afford chloroacylated polyacrylonitrile; 1 g of chloroacylated polyacrylonitrile was weighed and dissolved in 100 mL of DMF, 0.2 g of 4-amino benzo-15-crown-5 and 0.02 g of anhydrous potassium carbonate were added and uniformly blended; after reacting at a controlled temperature of 55° C. for 6 h, the reaction system was poured into methanol to precipitate. The precipitate was obtained by suction filtration. It is washed with methanol for several times and dried to afford crown ether grafted polyacrylonitrile polymeric material, wherein the loading amount of crown ether is 0.2 mmol/g. The graft polymeric material obtained by means of solid-liquid extraction between crown ether grafted polyacrylonitrile polymer and lithium chloride in methanol solution has a single-stage separation factor of 1.028 for lithium isotopes. The polymeric material obtained in the present example has a structure as follows:

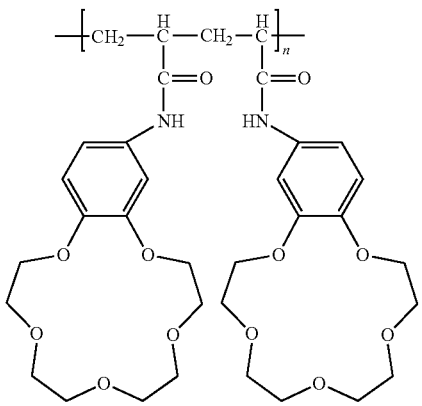

The examples mentioned above are regarded only as preferred embodiments of the present invention, the protective scope of the present invention is not limited thereto. Any modification or replacement in the technical scope disclosed in the present invention, which could be readily understood by those skilled in the art, shall fall within the protective scope of the present invention. Therefore, the protective scope of the present invention shall only be determined by the claims attached hereinafter.

What is claimed is:

1. A graft polymer with lithium isotopic separation effect, characterized in that the graft polymer comprises main chain and pendant group, taking a main chain of a polymer containing chloroformyl group or hydroxyl group as the main chain of the graft polymer, the pendant group is a benzocrown ether; the graft polymer is obtained by the reaction between a polymer containing chloroformyl group and benzocrown ether containing amino or hydroxyl functional group, or the graft polymer is obtained by the reaction between a polymer containing hydroxyl group and benzocrown ether containing carboxyl functional group; wherein in the graft polymer taking the main chain of the polymer containing hydroxyl group as the main chain of the graft polymer, the content of the pendant group is 0.1~3.0 mmol/g, in the graft polymer taking the main chain of the polymer containing chloroformyl group as the main chain of the graft polymer, the content of the pendant group is 0.1~2.0 mmol/g;

wherein the polymer containing chloroformyl group is polysulfone, polyether sulfone, polystyrene, polyacrylonitrile, or polyether-ether-ketone containing chloroformyl group, the polymer containing hydroxyl group is chitosan, chitin or cellulose with a hydroxyl substitution degree of lower than 3 in glucose unit.

2. The graft polymer with lithium isotopic separation effect according to claim 1, characterized in that the benzocrown ether is one of amino benzo macrocyclic crown ethers, hydroxyl benzo macrocyclic crown ethers and carboxyl benzo macrocyclic crown ethers, their general structures are shown as follows:

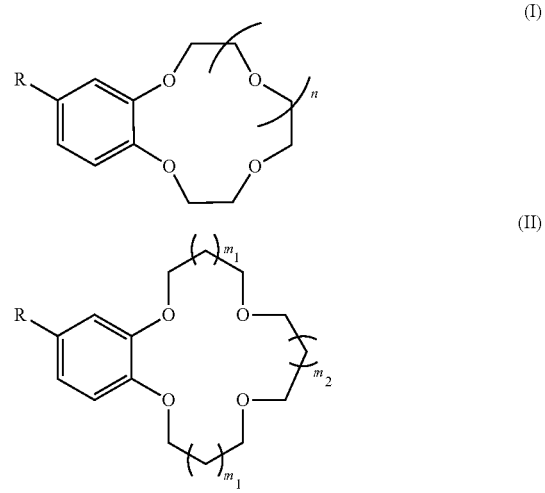

wherein n is equal to 1, 2, 3 or 4, $m_1$ and $m_2$ are equal to 0 or 1, in the graft polymer taking the main chain of a polymer containing chloroformyl group as main chain, R group is selected from the group consisting of —$NH_2$ and —OH, in the graft polymer taking the main chain of the polymer containing hydroxyl group as main chain, R group is selected from the group consisting of —COOH.

3. A preparation method of the graft polymer with lithium isotopic separation effect of claim 1, characterized in that firstly, preparing polymer solution with a certain concentration by dissolving a polymer containing chloroformyl group or hydroxyl group in a solvent; then blending a catalyst and a carboxyl benzocrown ether and dissolving in the polymer solution containing hydroxyl, covalently bonding the carboxyl benzocrown ether to the main chain of polymer by chemical grafting reaction at a certain temperature and for a certain time, or blending an acid-binding agent and an amino benzocrown ether or a hydroxyl benzocrown ether and dissolving in the polymer solution containing chloroformyl group, covalently bonding the amino benzocrown ether or the hydroxyl benzocrown ether to the main chain of polymer by SN1 reaction at a certain temperature and for a certain time, and precipitating the graft polymer from the polymer solution by using a precipitating agent to obtain the graft polymeric material, wherein the concentration of the polymer solution containing chloroformyl group is 10.0 g/L~100.0 g/L, the mass ratio of the polymer containing chloroformyl group to the amino benzocrown ether or the hydroxyl benzocrown ether is 1:1~5:1; the concentration of the polymer solution containing hydroxyl is 10.0 g/L~100.0 g/L, the mass ratio of the polymer containing hydroxyl to the carboxyl benzocrown ether is 0.1:1~5:1, the mass ratio of the polymer containing hydroxyl to the catalyst is 0.5:1~50:1.

4. The method according to claim 3, characterized in that the polymer containing chloroformyl group is polysulfone, polyether sulfone, polystyrene, polyacrylonitrile, or polyether-ether-ketone containing chloroformyl group, the polymer containing hydroxyl is chitosan, chitin or cellulose with a hydroxyl substitution degree of lower than 3 in glucose unit.

5. The method according to claim 3, characterized in that the general formula of the amino benzocrown ether, hydroxyl benzocrown ether or carboxyl benzocrown ether is shown as follows:

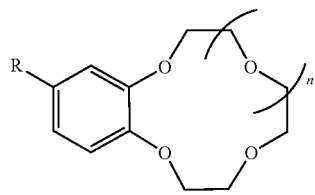

(I)

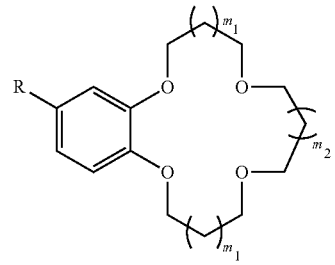

(II)

wherein n is equal to 1, 2, 3 or 4, $m_1$ and $m_2$ are equal to 0 or 1, R group is selected from the group consisting of —$NH_2$, —OH or —COOH.

6. The method according to claim 3, characterized in that the solvent for dissolving the polymer containing chloroformyl group is N,N-dimethyl formamide, 1,4-dioxane, dimethyl sulfoxide or N,N-dimethyl acetamide, the solvent for dissolving the polymer containing hydroxyl is distilled water or dimethyl sulfoxide.

7. The method according to claim 3, characterized in that the acid-binding agent is one of anhydrous potassium carbonate, anhydrous sodium carbonate, anhydrous sodium bicarbonate and triethylamine, the catalyst is one of concentrated sulfuric acid, concentrated hydrochloric acid, p-toluenesulfonic acid, $FeCl_3$, $SnCl_2$, $NaHSO_4$, $CuSO_4$ and dibutyl tin dilaurate.

8. The method according to claim 3, characterized in that the temperature of the SN1 reaction is 50~80° C., the reactive time thereof is 5~24 h; the temperature of the chemical grafting reaction is 50~130° C., the reactive time thereof is 1~24 h.

9. The method according to claim 3, characterized in that the precipitating agent is one of methanol, ethanol, n-butanol and acetone.

* * * * *